(12) United States Patent
Wood (10) Patent No.: US 8,425,428 B2
(45) Date of Patent: Apr. 23, 2013

(54) NITRIC OXIDE MEASUREMENTS IN PATIENTS USING FLOWFEEDBACK

(75) Inventor: Lockett E. Wood, Lyons, CO (US)

(73) Assignee: Covidien LP, Mansfield, MA (US)

( * ) Notice: Subject to any disclaimer, the term of this patent is extended or adjusted under 35 U.S.C. 154(b) by 734 days.

(21) Appl. No.: 12/404,995

(22) Filed: Mar. 16, 2009

(65) Prior Publication Data

US 2009/0247891 A1   Oct. 1, 2009

Related U.S. Application Data

(60) Provisional application No. 61/040,946, filed on Mar. 31, 2008.

(51) Int. Cl.
*A61B 5/02* (2006.01)

(52) U.S. Cl.
USPC ............ 600/532; 600/538; 600/540; 600/543

(58) Field of Classification Search .................. 600/532, 600/543; 73/23.3
See application file for complete search history.

(56) References Cited

U.S. PATENT DOCUMENTS

| | | | |
|---|---|---|---|
| 4,267,827 A | 5/1981 | Rauscher et al. |
| 4,752,089 A | 6/1988 | Carter |
| 4,770,168 A | 9/1988 | Rusz et al. |
| 4,921,642 A | 5/1990 | LaTorraca |
| 4,954,799 A | 9/1990 | Kumar |
| 5,057,822 A | 10/1991 | Hoffman |
| 5,072,737 A | 12/1991 | Goulding |
| 5,150,291 A | 9/1992 | Cummings et al. |
| 5,161,525 A | 11/1992 | Kimm et al. |
| 5,228,434 A | 7/1993 | Fishman |
| 5,237,987 A | 8/1993 | Anderson et al. |
| 5,271,389 A | 12/1993 | Isaza et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,307,795 A | 5/1994 | Whitwam et al. |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,355,893 A | 10/1994 | Mick et al. |

(Continued)

FOREIGN PATENT DOCUMENTS

| | | |
|---|---|---|
| DE | 3416291 | 3/1985 |
| DE | 4312431 | 4/1994 |

(Continued)

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Navin Natnithithadha
*Assistant Examiner* — Michael R Bloch (57) ABSTRACT

The present invention provides a method for measuring FeNO in a subject, wherein the FeNO data derived from a subject patient is normalized to compensate for variations of FeNO with flow rate.

13 Claims, 8 Drawing Sheets

U.S. PATENT DOCUMENTS

| | | | |
|---|---|---|---|
| 5,357,946 A | 10/1994 | Kee et al. | |
| 5,368,019 A | 11/1994 | LaTorraca | |
| 5,383,449 A | 1/1995 | Forare et al. | |
| 5,385,142 A | 1/1995 | Brady et al. | |
| 5,390,666 A | 2/1995 | Kimm et al. | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,438,980 A | 8/1995 | Phillips | |
| 5,443,075 A | 8/1995 | Holscher | |
| 5,485,835 A | 1/1996 | Vande Streek et al. | |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| 5,531,218 A | 7/1996 | Kreb | |
| 5,531,221 A | 7/1996 | Power | |
| 5,533,512 A | 7/1996 | Novotny et al. | |
| 5,542,415 A | 8/1996 | Brady | |
| 5,544,674 A | 8/1996 | Kelly | |
| 5,549,106 A | 8/1996 | Gruenke et al. | |
| 5,558,083 A | 9/1996 | Bathe et al. | |
| 5,579,774 A | 12/1996 | Miller et al. | |
| 5,596,984 A | 1/1997 | O'Mahoney et al. | |
| 5,630,411 A | 5/1997 | Holscher | |
| 5,632,270 A | 5/1997 | O'Mahoney et al. | |
| 5,645,048 A | 7/1997 | Brodsky et al. | |
| 5,651,358 A | 7/1997 | Briend et al. | |
| 5,660,171 A | 8/1997 | Kimm et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,697,364 A | 12/1997 | Chua et al. | |
| 5,715,812 A | 2/1998 | Deighan et al. | |
| 5,720,277 A | 2/1998 | Olsson et al. | |
| 5,732,693 A | 3/1998 | Bathe et al. | |
| 5,752,509 A | 5/1998 | Lachmann et al. | |
| 5,762,480 A | 6/1998 | Adahan | |
| 5,771,884 A | 6/1998 | Yarnall et al. | |
| 5,791,339 A | 8/1998 | Winter | |
| 5,794,986 A | 8/1998 | Gansel et al. | |
| 5,813,399 A | 9/1998 | Isaza et al. | |
| 5,826,575 A | 10/1998 | Lall | |
| 5,829,441 A | 11/1998 | Kidd et al. | |
| 5,836,300 A | 11/1998 | Mault | |
| 5,839,433 A | 11/1998 | Higenbottam | |
| 5,857,460 A | 1/1999 | Popitz | |
| 5,864,938 A | 2/1999 | Gansel et al. | |
| 5,865,168 A | 2/1999 | Isaza | |
| 5,871,009 A | 2/1999 | Rydgren et al. | |
| 5,881,717 A | 3/1999 | Isaza | |
| 5,881,723 A | 3/1999 | Wallace et al. | |
| 5,884,623 A | 3/1999 | Winter | |
| 5,909,731 A | 6/1999 | O'Mahoney et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,934,274 A | 8/1999 | Merrick et al. | |
| 6,010,459 A * | 1/2000 | Silkoff et al. | 600/532 |
| 6,024,089 A | 2/2000 | Wallace et al. | |
| 6,029,660 A | 2/2000 | Calluaud et al. | |
| 6,041,780 A | 3/2000 | Richard et al. | |
| 6,047,860 A | 4/2000 | Sanders | |
| 6,076,523 A | 6/2000 | Jones et al. | |
| 6,089,229 A | 7/2000 | Bathe et al. | |
| 6,099,481 A | 8/2000 | Daniels et al. | |
| 6,109,260 A | 8/2000 | Bathe | |
| 6,116,240 A | 9/2000 | Merrick et al. | |
| 6,116,464 A | 9/2000 | Sanders | |
| 6,123,072 A | 9/2000 | Downs | |
| 6,123,073 A | 9/2000 | Schlawin et al. | |
| 6,125,846 A | 10/2000 | Bathe et al. | |
| 6,131,571 A | 10/2000 | Lampotang et al. | |
| 6,135,105 A | 10/2000 | Lampotang et al. | |
| 6,135,106 A | 10/2000 | Dirks et al. | |
| 6,135,107 A | 10/2000 | Mault | |
| 6,142,147 A | 11/2000 | Head et al. | |
| 6,142,150 A | 11/2000 | O'Mahoney | |
| 6,161,539 A | 12/2000 | Winter | |
| 6,164,276 A | 12/2000 | Bathe et al. | |
| 6,179,784 B1 | 1/2001 | Daniels et al. | |
| 6,200,271 B1 | 3/2001 | Kück et al. | |
| 6,210,342 B1 | 4/2001 | Kück et al. | |
| 6,220,245 B1 | 4/2001 | Takabayashi et al. | |
| 6,236,041 B1 | 5/2001 | Donnerhack et al. | |
| 6,238,351 B1 | 5/2001 | Orr et al. | |
| 6,258,038 B1 | 7/2001 | Haryadi et al. | |
| 6,269,812 B1 | 8/2001 | Wallace et al. | |
| 6,273,444 B1 | 8/2001 | Power | |
| 6,283,119 B1 | 9/2001 | Bourdon | |
| 6,305,373 B1 | 10/2001 | Wallace et al. | |
| 6,321,748 B1 | 11/2001 | O'Mahoney | |
| 6,325,785 B1 | 12/2001 | Babkes et al. | |
| 6,357,438 B1 | 3/2002 | Hansen | |
| 6,360,745 B1 | 3/2002 | Wallace et al. | |
| 6,369,838 B1 | 4/2002 | Wallace et al. | |
| 6,412,483 B1 | 7/2002 | Jones et al. | |
| 6,439,229 B1 | 8/2002 | Du et al. | |
| 6,439,234 B1 | 8/2002 | Curti et al. | |
| 6,467,478 B1 | 10/2002 | Merrick et al. | |
| 6,471,658 B1 | 10/2002 | Daniels et al. | |
| 6,536,429 B1 | 3/2003 | Pavlov et al. | |
| 6,546,930 B1 | 4/2003 | Emerson et al. | |
| 6,553,991 B1 | 4/2003 | Isaza | |
| 6,557,553 B1 | 5/2003 | Borrello | |
| 6,571,795 B2 | 6/2003 | Bourdon | |
| 6,581,592 B1 | 6/2003 | Bathe et al. | |
| 6,581,599 B1 | 6/2003 | Stenzler | |
| 6,616,615 B2 | 9/2003 | Mault et al. | |
| 6,622,726 B1 | 9/2003 | Du | |
| 6,629,934 B2 | 10/2003 | Mault et al. | |
| 6,644,310 B1 | 11/2003 | Delache et al. | |
| 6,648,831 B2 | 11/2003 | Orr et al. | |
| 6,648,832 B2 | 11/2003 | Orr et al. | |
| 6,655,385 B1 | 12/2003 | Curti et al. | |
| 6,668,824 B1 | 12/2003 | Isaza et al. | |
| 6,675,801 B2 | 1/2004 | Wallace et al. | |
| 6,718,974 B1 | 4/2004 | Moberg | |
| 6,725,447 B1 | 4/2004 | Gilman et al. | |
| 6,739,337 B2 | 5/2004 | Isaza | |
| 6,758,214 B2 | 7/2004 | Fine et al. | |
| 6,761,167 B1 | 7/2004 | Nadjafizadeh et al. | |
| 6,761,168 B1 | 7/2004 | Nadjafizadeh et al. | |
| 6,786,217 B2 | 9/2004 | Stenzler | |
| 6,814,074 B1 | 11/2004 | Nadjafizadeh et al. | |
| 6,860,266 B2 | 3/2005 | Blike | |
| 6,866,040 B1 | 3/2005 | Bourdon | |
| 6,871,645 B2 | 3/2005 | Wartman et al. | |
| 6,884,222 B1 | 4/2005 | Braig | |
| 6,935,336 B2 | 8/2005 | Lurie et al. | |
| 6,938,618 B2 | 9/2005 | Lurie et al. | |
| 6,955,651 B2 | 10/2005 | Kück et al. | |
| 6,960,854 B2 | 11/2005 | Nadjafizadeh et al. | |
| 6,990,977 B1 | 1/2006 | Calluaud et al. | |
| 6,997,880 B2 | 2/2006 | Carlebach et al. | |
| 7,018,340 B2 | 3/2006 | Jaffe et al. | |
| 7,024,235 B2 | 4/2006 | Melker et al. | |
| 7,025,869 B2 | 4/2006 | Fine et al. | |
| 7,036,504 B2 | 5/2006 | Wallace et al. | |
| 7,040,313 B2 | 5/2006 | Fine et al. | |
| 7,070,566 B2 | 7/2006 | Medero et al. | |
| 7,070,569 B2 | 7/2006 | Heinonen et al. | |
| 7,070,570 B2 | 7/2006 | Sanderson et al. | |
| 7,077,131 B2 | 7/2006 | Hansen | |
| RE39,225 E | 8/2006 | Isaza et al. | |
| 7,108,666 B2 | 9/2006 | Stenzler | |
| 7,117,438 B2 | 10/2006 | Wallace et al. | |
| 7,152,604 B2 | 12/2006 | Hickle et al. | |
| 7,185,649 B2 | 3/2007 | Lurie | |
| 7,195,012 B2 | 3/2007 | Lurie | |
| 7,207,947 B2 | 4/2007 | Koh et al. | |
| 7,210,480 B2 | 5/2007 | Lurie et al. | |

| | | |
|---|---|---|
| 7,225,022 B2 | 5/2007 | Anderson et al. |
| 7,270,126 B2 | 9/2007 | Wallace et al. |
| 7,273,050 B2 | 9/2007 | Wei |
| 7,275,542 B2 | 10/2007 | Lurie et al. |
| 7,335,164 B2 | 2/2008 | Mace et al. |
| 7,335,181 B2 | 2/2008 | Miller et al. |
| 7,369,757 B2 | 5/2008 | Farbarik |
| 7,370,650 B2 | 5/2008 | Nadjafizadeh et al. |
| 7,387,123 B2 | 6/2008 | DeSilva et al. |
| 7,425,201 B2 | 9/2008 | Euliano et al. |
| 7,428,902 B2 | 9/2008 | Du et al. |
| 7,438,072 B2 | 10/2008 | Izuchukwu |
| 7,455,062 B2 | 11/2008 | Roehl et al. |
| 7,460,959 B2 | 12/2008 | Jafari |
| 7,487,773 B2 | 2/2009 | Li |
| 7,516,742 B2 | 4/2009 | Stenzler et al. |
| 7,588,543 B2 | 9/2009 | Euliano et al. |
| 7,654,802 B2 | 2/2010 | Crawfor, Jr. et al. |
| 7,694,677 B2 | 4/2010 | Tang |
| 7,717,113 B2 | 5/2010 | Andrieux |
| 7,779,834 B2 | 8/2010 | Calluaud et al. |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,984,714 B2 | 7/2011 | Hausmann et al. |
| 7,992,557 B2 | 8/2011 | Nadjafizadeh et al. |
| 8,001,967 B2 | 8/2011 | Wallace et al. |
| 8,021,310 B2 | 9/2011 | Sanborn et al. |
| 8,181,648 B2 | 5/2012 | Perine et al. |
| 8,210,173 B2 | 7/2012 | Vandine |
| 8,210,174 B2 | 7/2012 | Farbarik |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2002/0029003 A1 | 3/2002 | Mace |
| 2002/0069877 A1 | 6/2002 | Villareal et al. |
| 2002/0087057 A1 | 7/2002 | Lovejoy et al. |
| 2002/0193698 A1* | 12/2002 | Moilanen et al. ............ 600/532 |
| 2003/0045807 A1 | 3/2003 | Daniels, II et al. |
| 2003/0062040 A1 | 4/2003 | Lurie et al. |
| 2003/0070678 A1 | 4/2003 | Wartman et al. |
| 2003/0106553 A1 | 6/2003 | Vanderveen |
| 2003/0106554 A1 | 6/2003 | De Silva et al. |
| 2003/0208131 A1* | 11/2003 | George ........................ 600/532 |
| 2003/0225339 A1 | 12/2003 | Orr et al. |
| 2004/0040560 A1 | 3/2004 | Euliano et al. |
| 2004/0045552 A1 | 3/2004 | Curti et al. |
| 2004/0082872 A1* | 4/2004 | von Bahr et al. ............ 600/532 |
| 2004/0116784 A1 | 6/2004 | Gavish |
| 2004/0144383 A1 | 7/2004 | Thomas et al. |
| 2004/0254482 A1 | 12/2004 | Anderson et al. |
| 2005/0039748 A1 | 2/2005 | Andrieux |
| 2005/0109340 A1 | 5/2005 | Tehrani |
| 2005/0112325 A1 | 5/2005 | Hickle |
| 2005/0137645 A1 | 6/2005 | Voipio et al. |
| 2005/0139212 A1 | 6/2005 | Bourdon |
| 2005/0139213 A1 | 6/2005 | Blike |
| 2005/0215844 A1 | 9/2005 | Ten Eyck et al. |
| 2005/0217671 A1 | 10/2005 | Fisher et al. |
| 2005/0247311 A1 | 11/2005 | Vacchiano et al. |
| 2005/0251214 A1 | 11/2005 | Parascandola et al. |
| 2005/0284476 A1 | 12/2005 | Blanch et al. |
| 2005/0284484 A1 | 12/2005 | Curti et al. |
| 2006/0129054 A1 | 6/2006 | Orr et al. |
| 2006/0189880 A1 | 8/2006 | Lynn et al. |
| 2006/0225737 A1 | 10/2006 | Iobbi |
| 2006/0231098 A1 | 10/2006 | Downie et al. |
| 2006/0249151 A1 | 11/2006 | Gambone |
| 2006/0253038 A1 | 11/2006 | Kuck et al. |
| 2007/0017515 A1 | 1/2007 | Wallace et al. |
| 2007/0034208 A1 | 2/2007 | Roehl et al. |
| 2007/0044799 A1 | 3/2007 | Hete et al. |
| 2007/0053992 A1 | 3/2007 | Abraini et al. |
| 2007/0062531 A1 | 3/2007 | Fisher et al. |
| 2007/0068518 A1 | 3/2007 | Urias et al. |
| 2007/0073170 A1 | 3/2007 | Danehorn et al. |
| 2007/0077200 A1 | 4/2007 | Baker |
| 2007/0107728 A1 | 5/2007 | Ricciardelli et al. |
| 2007/0129666 A1 | 6/2007 | Barton et al. |
| 2007/0149891 A1 | 6/2007 | George et al. |
| 2007/0151561 A1 | 7/2007 | Laurila |
| 2007/0157931 A1 | 7/2007 | Parker et al. |
| 2007/0181126 A1 | 8/2007 | Tolmie et al. |
| 2007/0221222 A1 | 9/2007 | Lurie |
| 2007/0225612 A1 | 9/2007 | Mace et al. |
| 2007/0227537 A1 | 10/2007 | Bemister et al. |
| 2007/0232951 A1 | 10/2007 | Euliano et al. |
| 2007/0255160 A1 | 11/2007 | Daly |
| 2007/0272243 A1 | 11/2007 | Sherman et al. |
| 2007/0277823 A1 | 12/2007 | Al-Ali et al. |
| 2007/0284361 A1 | 12/2007 | Nadjafizadeh et al. |
| 2008/0029091 A1 | 2/2008 | Mullner |
| 2008/0039735 A1 | 2/2008 | Hickerson |
| 2008/0053441 A1 | 3/2008 | Gottlib et al. |
| 2008/0072896 A1 | 3/2008 | Setzer et al. |
| 2008/0072902 A1 | 3/2008 | Setzer et al. |
| 2008/0078304 A1 | 4/2008 | Milne et al. |
| 2008/0083644 A1 | 4/2008 | Janbakhsh et al. |
| 2008/0087284 A1 | 4/2008 | Krueger et al. |
| 2008/0092894 A1 | 4/2008 | Nicolazzi et al. |
| 2008/0097234 A1 | 4/2008 | Nicolazzi et al. |
| 2008/0194980 A1 | 8/2008 | Gisolf et al. |
| 2008/0202526 A1 | 8/2008 | Heinonen |
| 2008/0230065 A1 | 9/2008 | Heinonen |
| 2008/0236581 A1 | 10/2008 | Rantala et al. |
| 2008/0236582 A1 | 10/2008 | Tehrani |
| 2008/0275340 A1 | 11/2008 | Beach et al. |
| 2008/0295839 A1 | 12/2008 | Habashi |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2010/0011307 A1 | 1/2010 | Desfossez et al. |
| 2010/0024820 A1 | 2/2010 | Bourdon |
| 2010/0071689 A1 | 3/2010 | Thiessen |
| 2010/0071695 A1 | 3/2010 | Thiessen |
| 2010/0071696 A1 | 3/2010 | Jafari |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0218765 A1 | 9/2010 | Jafari et al. |
| 2010/0218766 A1 | 9/2010 | Milne |
| 2010/0218767 A1 | 9/2010 | Jafari et al. |

FOREIGN PATENT DOCUMENTS

| | | |
|---|---|---|
| DE | 19701617 | 7/1998 |
| FR | 2850874 | 8/2004 |
| WO | WO9710869 | 3/1997 |
| WO | WO9831282 | 7/1998 |
| WO | WO2008012350 | 1/2008 |

OTHER PUBLICATIONS

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

7200 Ventilatory System: Addendum/Errata. Nellcor Puritan Bennett, Part No. 4-023576-00, Rev. A, Apr. 1998, pp. 1-32.

Deyken et al., *Amer. J. Resp. and Crit. Care Med.*, (2002) 165:1597-1601.

* cited by examiner

FIG. 1

PRIOR ART

NITRIC OXIDE MEASUREMENTS IN PATIENTS USING FLOWFEEDBACK

CROSS-REFERENCE TO RELATED APPLICATION

This claims the benefit of U.S. Provisional Patent Application No. 61/040,946, filed Mar. 31, 2008, which is hereby incorporated by reference herein in its entirety.

BACKGROUND

Asthma is a chronic disease with no known cure. Substantial alleviation of asthma symptoms is possible via preventive therapy, such as the use of bronchodilators and anti-inflammatory agents. Asthma management is aimed at improving the quality of life of asthma patients. Asthma management presents a serious challenge to the patient and physician, as preventive therapies require constant monitoring of lung function and corresponding adaptation of medication type and dosage. However, monitoring of lung function is not simple, and requires sophisticated instrumentation and expertise, which are generally not available in the non-clinical or home environment.

Monitoring of lung function is viewed as a major factor in determining an appropriate treatment, as well as in patient follow-up. Preferred therapies are often based on aerosol-type medications to minimize systemic side-effects. The efficacy of aerosol type therapy is highly dependent on patient compliance, which is difficult to assess and maintain, further contributing to the importance of lung-function monitoring.

Asthma episodes usually develop over a period of several days, although they may sometimes seem to appear unexpectedly. The gradual onset of the asthmatic episode provides an opportunity to start countermeasures to stop and reverse the inflammatory process. Early treatment at the pre-episode stage may reduce the clinical episode manifestation considerably, and may even prevent the transition from the pre-clinical stage to a clinical episode altogether.

Two techniques are generally used for asthma monitoring. The first technique, spirometry, evaluates lung function using a spirometer, an instrument that measures the volume of air inhaled and exhaled by the lungs. Airflow dynamics are measured during a forceful, coordinated inhalation and exhalation effort by the patient into a mouthpiece connected via a tube to the spirometer. A peak-flow meter is a simpler device that is similar to the spirometer, and is used in a similar manner. The second technique evaluates lung function by measuring nitric-oxide concentration using a dedicated nitric-oxide monitor. The patient breathes into a mouthpiece connected via a tube to the monitor.

However, the measurement of FeNO (exhaled nitric oxide) is subject to significant measurement variation. For example, the concentration of NO in exhaled breath is dependent upon the exhalation rate. This variability is a major limitation in the clinical application of FeNO measurements.

SUMMARY

The disclosure provides a method for measuring FeNO (exhaled NO concentration in ppb) in a subject, wherein the FeNO data derived from a subject patient is normalized to compensate for variations of FeNO due to different exhalation flow rates. In one embodiment, the method comprises:
  a. causing a subject to exhale into an apparatus for receiving exhaled breath;
  b. measuring FeNO;
  c. measuring the flow rate of exhaled breath as a function of time;
  d. correlating the measured FeNO and flow rates to generate FeNO data as a function of time;
  e. for a selected flow rate, identifying an FeNO value corresponding to the selected flow rate;
  f. calculating a baseline correction factor "X" according to the formula: $X=A/B$ where A is the average FeNO identified in step e; and B is FeNO for a normal subject;
  g. normalizing the generated FeNO data using the baseline correction factor X;
  h. adjusting the normalized FeNO data to the selected flow rate; and
  i. scaling back the normalized FeNO data using the baseline correction factor.

In a particular embodiment, the selected flow rate is about 50 ml/sec, as set forth in ATS (American Thoracic Society) guidelines. Preferably, the subject is caused to exhale at a substantially constant flow rate, for example, at a rate of about 50 ml/sec±10 ml/sec. Typically, the normal subject FeNO ("B") is also determined using ATS standards.

The invention further provides a method of calibrating FeNO data derived from a subject, the method comprising the steps:
  a. plotting flow rate of exhaled breath as a function of time;
  b. correlating a measured FeNO value and the flow rate as a function of time;
  c. plotting FeNO as a function of time based on the correlating operation;
  d. selecting a flow rate, and identifying each FeNO corresponding to the selected flow rate;
  e. calculating a baseline correction factor "X" according to the formula: $X=A/B$ where A is the average FeNO and B is FeNO for a normal subject;
  f. normalizing the FeNO as a function of time using the baseline correction factor X to obtain normalized FeNO data;
  g. adjusting the normalized FeNO data to the selected flow rate; and
  h. scaling back the normalized FeNO data using the baseline correction factor.

The invention also provides an NO monitoring system comprising a data storage module for storing FeNO and flow rate data points; and a normalization module for normalizing FeNO data points. The normalization module may use an algorithm for normalizing FeNO data points. According to one embodiment, the algorithm:
  a. plots flow rate of exhaled breath as a function of time;
  b. correlates a measured FeNO and the plot of the flow rate to obtain estimated FeNO data as a function of time;
  c. plots FeNO as a function of time based on the correlation;
  d. using a pre-selected a flow rate, identifies each FeNO corresponding to the selected flow rate;
  e. calculates a baseline correction factor "X" according to the formula: $X=A/B$ where A is the average FeNO and B is FeNO for a normal subject;
  f. normalizes the estimated FeNO data using the baseline correction factor X to obtain normalized FeNO data;
  g. adjusts the normalized FeNO data to the selected flow rate; and
  h. scales back the normalized FeNO data using the baseline correction factor.

In an embodiment, the NO monitoring system further comprises a means for detecting FeNO, such as an NO sensor. Typically, the NO monitoring system will further comprise a means for receiving exhaled breath from a subject; and means for measuring FeNO and exhalation rate as a function of time.

In yet another embodiment, the disclosure describes a method for measuring FeNO in a subject, in which the method comprises:
 a. during an exhalation by a subject, concurrently measuring the FeNO concentration in the exhaled breath and exhalation flow rate; and
 b. for any FeNO concentration measurements obtained when the exhalation flow rate is different from a target flow rate, correcting the FeNO concentration measurement based on the difference between the exhalation flow rate and the target flow rate and also based on predetermined information describing the relationship between FeNO concentration measurements and exhalation flow rate for a healthy subject.

In yet another embodiment, the disclosure describes a method for measuring FeNO in a subject, in which the method comprises:
 a. causing a subject to exhale into an apparatus for receiving exhaled breath;
 b. collecting at least some of the exhaled breath;
 c. measuring FeNO in the collected exhaled breath;
 d. measuring the flow rate of exhaled breath as a function of time;
 e. determining an average flow rate of the exhaled breath from the measured flow rate of exhaled breath as a function of time;
 f. calculating a baseline correction factor "X" according to the formula: X=A/B where A is the measured FeNO; and B is FeNO for a normal subject at the average flow rate;
 g. normalizing the measured FeNO using the baseline correction factor X to obtain a normalized FeNO;
 h. adjusting the normalized FeNO to a selected flow rate;
 i. scaling back the normalized FeNO using the baseline correction factor;
 j. thereby measuring FeNO in a subject.

In yet another embodiment, the disclosure describes a method for measuring FeNO in a subject, in which the method comprises:
 a. measuring FeNO concentration in an exhaled breath of the patient and the exhalation flow rate of the exhaled breath as a function of time;
 b. calculating a baseline correction factor based on the measured exhalation flow rate as a function of time, the measured FeNO, and predetermined information describing the relationship between FeNO concentration measurements and exhalation flow rate for a healthy patient; and
 c. determining an adjusted FeNO concentration at a target flow rate using the baseline correction factor, the measured FeNO concentration, and the predetermined information describing the relationship between FeNO concentration measurements and exhalation flow rate for a healthy patient.

DETAILED DESCRIPTION

The present invention provides a method for calibrating FeNO measurements obtained from a subject by adjusting the measurements to compensate for variations in FeNO with flow rate. In an embodiment, the invention involves use of an algorithm or look up table which normalizes and adjusts the data based on published FeNO variability data (see for, example, FIG. 1; Deyken et al., Amer. J. Resp. and Crit. Care Med., (2002) 165:1597-1601; incorporated herein by reference). The Deyken reference discloses a graphic depiction of FeNO concentrations versus flow rates for normal patients (i.e., those with unimpaired lung function). This graph is used to derive correction factors to normalize the data derived from a patient. Thus, an embodiment of the method described herein could be considered correcting FeNO concentration measurements based on both a) the difference between an exhalation flow rate and a target flow rate, and b) predetermined information such as the curve in FIG. 1 describing the relationship between FeNO concentration measurements and exhalation flow rate for a healthy subject.

Figure 7:
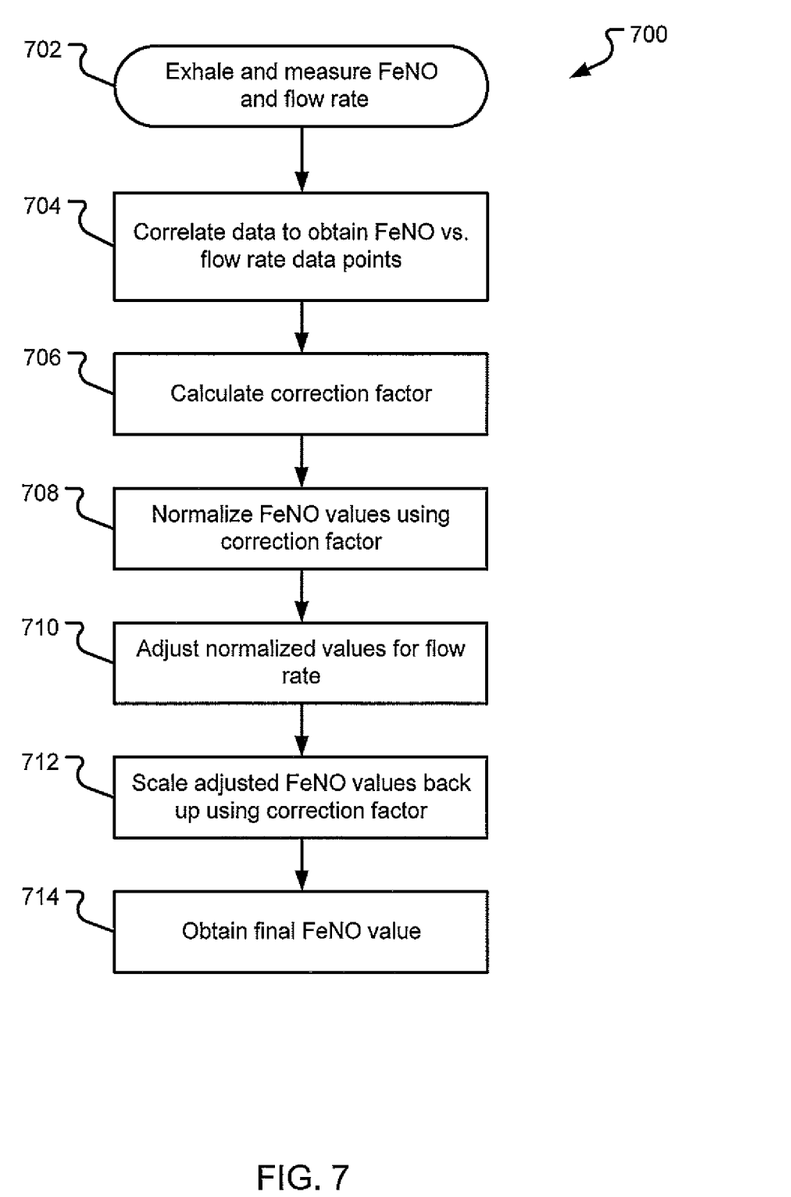
FIG. 7 is a flowchart illustrating some of the operations in an embodiment of a method for measuring FeNO in a subject.

FIG. 7 is a flowchart illustrating some of the operations in an embodiment of a method for measuring FeNO in a subject. The method 700 involves causing a subject to exhale into an apparatus or device for receiving exhaled breath, as illustrated by the exhalation operation 702. According to published ATS standards, the subject should exhale at a substantially constant rate of 50 ml/sec. While the methods of the invention described herein allow for any flow rate, it is preferable that the subject attempt to keep within the published guidelines, and the algorithm be used to compensate for flow rate variability within a target range of 50 ml/sec., such as, for example, 40 to 60 ml/sec. It is contemplated that other ranges may be used, such as, for example, ±0.5; ±1; ±5; ±10; ±15; ±20 ml/sec; etc, of a selected target rate. It will be understood that the target rate may change based on subsequent studies of the optimum flow rate for diagnosing conditions using FeNO as an indicator.

During the exhalation operation 702, the flow rate of the exhalation is measured as a function of time. The flow rate data may be recorded, graphed or plotted for output or display purposes.

In addition, the exhalation operation 702 includes measuring the FeNO concentration in the exhaled breath and determining from the measurement(s) the FeNO in the exhaled breath as a function of time. In embodiments, the FeNO in the exhaled breath may be measured in various ways. One method is to perform an "on-line" measurement in which FeNO is directly measured in the exhaled breath as a function of time. This may be done by using a fast responding real-time NO sensor. Alternatively, the same result could be achieved by collecting multiple samples of the breath at different times, storing them in separate collection chambers such as sample containment bags, and analyzing them separately to obtain the different measurements.

For an off-line measurement system, all or some portion of the exhaled breath may be collected in a bag or other collection container. The breath is collected during the measurement of flow rate as discussed below. After collection, the sample is subsequently analyzed in an NO analyzer to obtain a single measurement of FeNO. The measured FeNO concentration of the sample represents the average FeNO for the duration of the exhalation.

The measured FeNO value can be used directly as an average value, or converted into FeNO data as a function of time. At correlate operation 704, in order to obtain FeNO data as a function of time, the measured FeNO value is correlated with the flow rate data to generate the FeNO data as a function of time and a plot of FeNO over time. In an embodiment, this is done using the normal curve of FIG. 1 to account for the known variations in exhaled FeNO as a function of flow rate. In alternative embodiments, one or more different curves/algorithms obtained from different sources may be used to extrapolate or otherwise estimate the FeNO as a function of time. Other methods of extrapolating an average FeNO from flow rate data to obtain FeNO values over time may also be used. For the purposes of this disclosure, any method of generating FeNO data as a function of time from an FeNO measurement and flow rate data, now known or later developed, may be used.

In an embodiment that uses the measured FeNO value as an average value, the remaining operations are performed on this single measured FeNO value. In an embodiment that uses FeNO data as function of time, the remaining operations may be performed for some or all of the FeNO data.

Regardless of the means and methods of obtaining the FeNO data, the FeNO data may be recorded, graphed and/or plotted for output or display purposes.

Next, a correction factor is calculated for the FeNO values in a correction factor determination operation 706. This operation 706 includes selecting a flow rate to determine the correction factor for adjusting the FeNO data point (if only one) or data points. This flow rate may be any value, but in an embodiment will be the target flow rate set forth in the published ATS standards. As of the time of filing, this flow rate is 50 ml/sec. Referring to the two plots of synchronized data, for each value of 50 ml/sec (or other selected target flow rate) on the collected flow rate data graph, the corresponding FeNO value is selected from the collected FeNO data graph as a representative FeNO value. If there is more than one FeNO value at 50 ml/sec, these FeNO values are then averaged to obtain a representative FeNO at the target flow rate. If no FeNO values were obtained at or near the target flow rate, a representative value may be determined by averaging one or more FeNO values within a specific range around the target flow rate.

In the correction factor determination operation 706, if only one FeNO value, e.g., the measured FeNO, is used rather than FeNO data as a function of time, the correction factor may be determined based on the measured flow rate information. For example, in an embodiment the average flow rate of the exhalation may be calculated from the flow rate data and the average used to determine the correction factor for adjusting the measured FeNO value.

Figure 1:
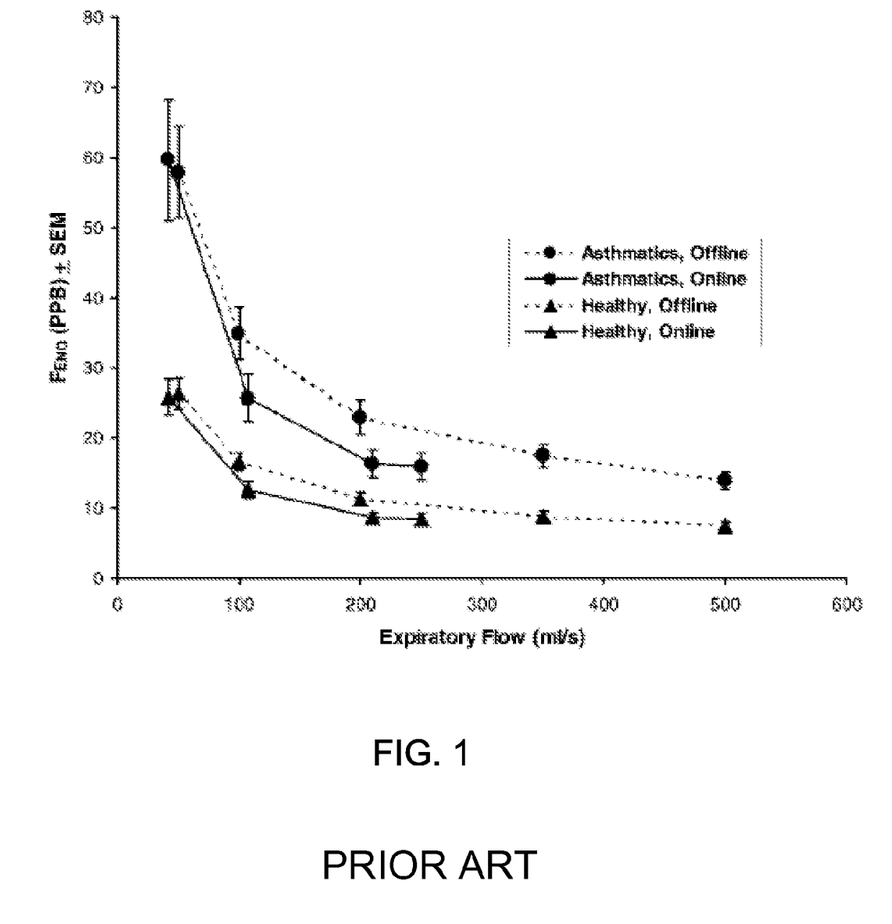
FIG. 1 is a schematic showing FeNO versus flow rate as set forth in Deykin et al.

In a next step, the FeNO for a normal subject at the target flow rate is determined. This may be done by referring to FIG. 1 of the Deykin reference or other similar source or lookup table. The representative FeNO value for the subject patient is then divided by the normal FeNO value. Accordingly, the baseline correction factor X is determined:

$X=A/B$ wherein X is the baseline correction factor; A is the average FeNO determined above; and B is FeNO for a normal subject.

The measured FeNO data are then scaled down or normalized using the baseline correction factor X in a normalization operation 708. In this operation 708, each FeNO concentration data point is divided by the correction factor X to obtain a set of normalized FeNO data points.

The normalized FeNO data are adjusted to compensate for the variations of FeNO with flow rate in an adjustment operation 710. This is done by, for each normalized FeNO data point, adjusting the FeNO value to its corresponding value at the target flow rate using the curve identified in FIG. 1.

For example, if a normalized data point is found to be on the curve in FIG. 1, then the value is adjusted to 25 ppb FeNO, which is where the curve intersects with the target 50 ml/sec flow rate. If the normalized data point is not on the curve, the curve is raised or lowered until the data point is on the curve and the value is adjusted to the FeNO concentration that intersects the raised or lowered curve at the target flow rate. In an alternative embodiment, rather than raising or lowering the curve, each normalized data point may be compared to the curve to determine a difference in FeNO concentration at the data point's flow rate, and this difference is then added to the 25 ppb FeNO to obtain the adjusted value at the target flow rate. In an alternative embodiment, a different curve may be used than that identified in FIG. 1.

It should be noted that the values of the FeNO data points taken at 50 ml/sec will ultimately not be changed by this method. Depending on the embodiment, these data points may be omitted from the calculations and their raw values used. Alternatively, all data points may be treated in the same manner regardless of their corresponding measured flow rate.

Once each normalized FeNO value has been adjusted to the target flow rate, the data is then "scaled back" by multiplying these adjusted FeNO values by the baseline correction factor X in a scaling operation 712. This results in a set of one or more FeNO values in which all values were either taken at the target flow rate or have been adjusted to the target flow rate.

The set of adjusted FeNO values, if there is more than one FeNO value in the set, may then be averaged or otherwise used to generate a final FeNO concentration for the patient at the target flow rate. This is illustrated by the final value calculation operation 714. If there is only one FeNO value, e.g., the measured FeNO is used rather than FeNO data as a function of time, the final value calculation operation 714 is unnecessary as the results of the scaling operation 712 will be the final FeNO value at the target flow rate.

Figure 2:
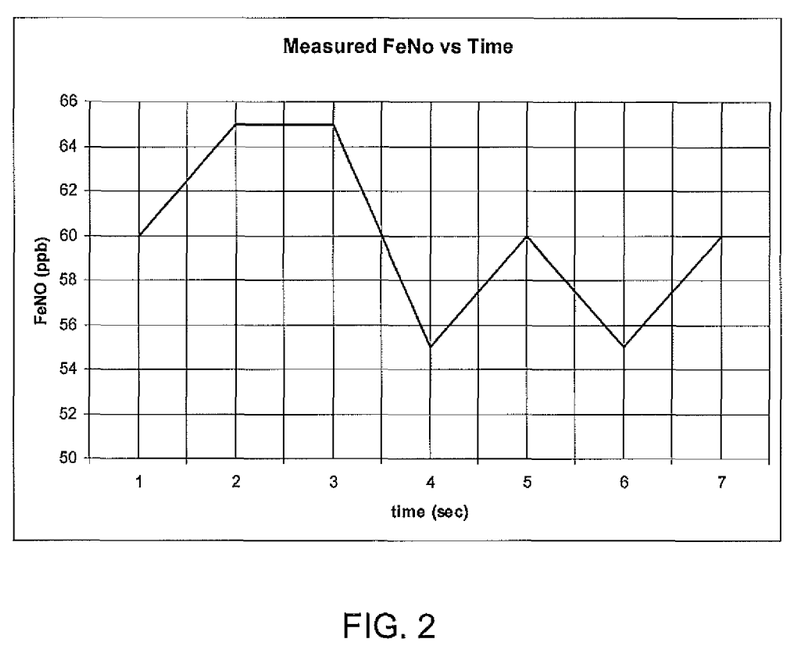
FIG. 2 is a schematic showing FeNO versus time for a hypothetical subject.
Figure 3:
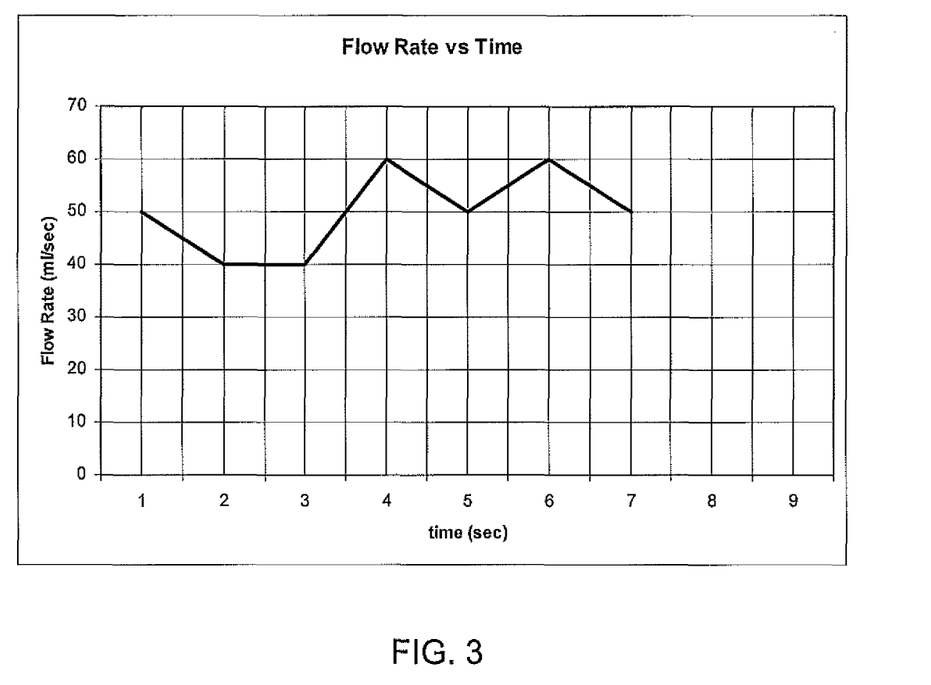
FIG. 3 is a schematic showing flow rate versus time for a hypothetical subject.

By way of example, FIG. 2 is a graph of FeNO (ppb) vs. time for a hypothetical patient, FIG. 3 represents exhalation flow rates over the same time period. As can been seen, when the Figures are synchronized or aligned based on time, as flow rate decreases the FeNO value increases. For a target flow rate of 50 ml/sec, all corresponding FeNO values are identified as described above in the correction factor operation 706. For example, in FIG. 3, at time=1 second, the flow rate is 50 ml/sec. The corresponding value in FIG. 2 is 60 ppb. All such FeNO values taken at 50 ml/sec are similarly identified and averaged. In this particular example, the representative FeNO is determined to be 60 ppb.

Referring to FIG. 1, the FeNO is 25 ppb at a flow rate of 50 ml/sec for a normal patient. The correction factor X is determined by dividing the average FeNO by the normal FeNO value. Thus, for X=A/B, 60/25 yields a correction factor of 2.4. All FeNO values are now divided by this correction factor X to yield a normalized set of FeNO values (FIG. 4).

Figure 4:
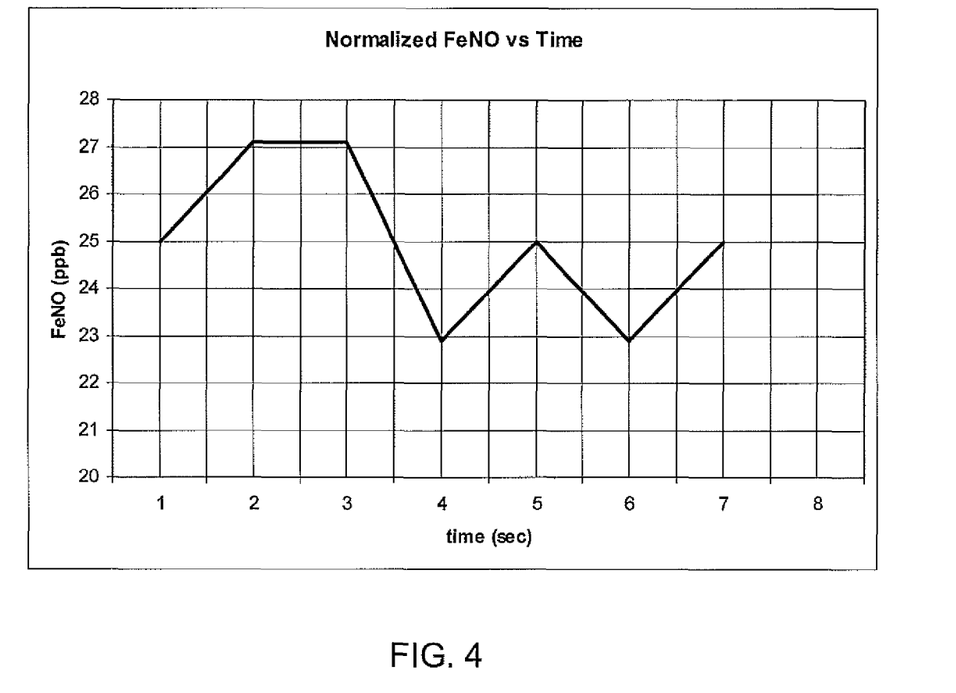
FIG. 4 is a schematic showing FeNO versus time normalized using baseline correction factor.
Figure 5:
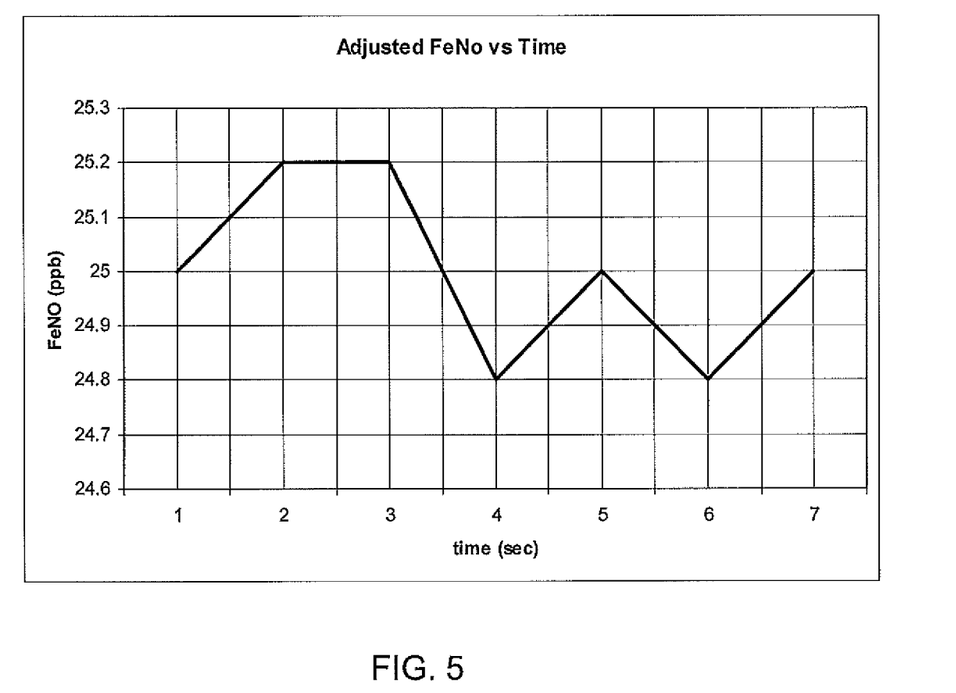
FIG. 5 is a schematic showing FeNO versus time adjusted for the selected target flow rate of 50 ml/sec.
Figure 6:
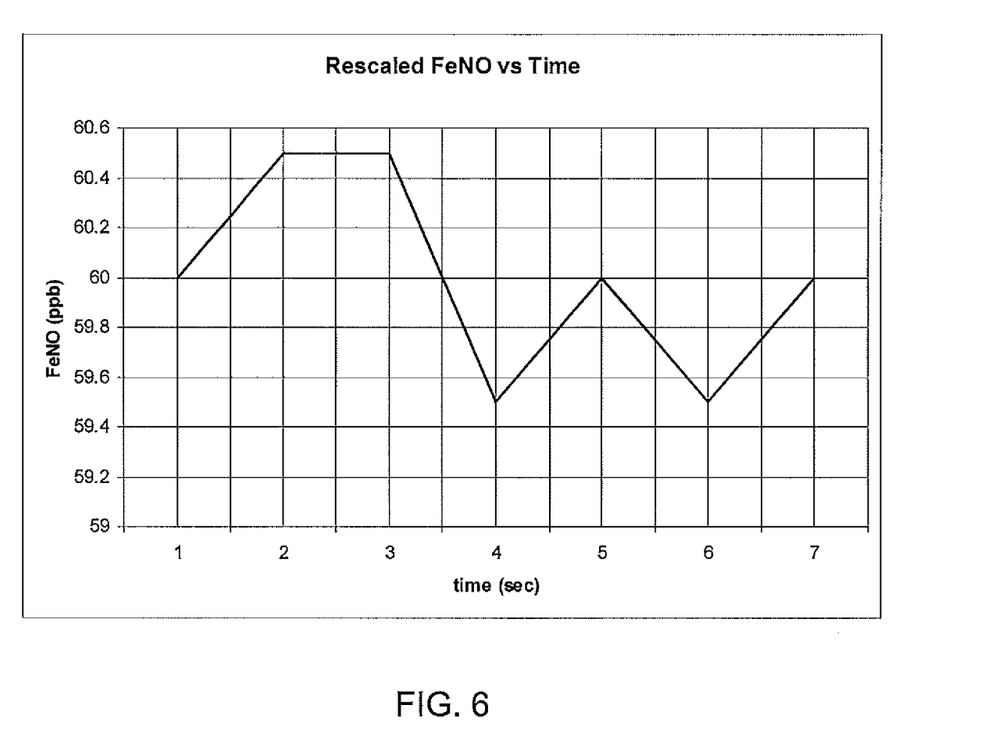
FIG. 6 is a schematic showing FeNO versus time re-scaled using the baseline correction factor.

For all values of FeNO in FIG. 4 which are not based on a flow rate of 50 ml/sec, FIG. 1 is used to determine the corresponding FeNO. In other words, for each such FeNO value, the curve in FIG. 1 is used to determine the FeNO value at 50 ml/seq. In this manner, an adjusted FeNO vs. time plot may be generated (FIG. 5). Finally, the adjusted values are scaled back to the original subject data by multiplying each value by the correction factor X (FIG. 6). The values are then averaged yielding the FeNO concentration for the subject patient. This value can then be used for diagnostic or other purposes.

Figure 8:
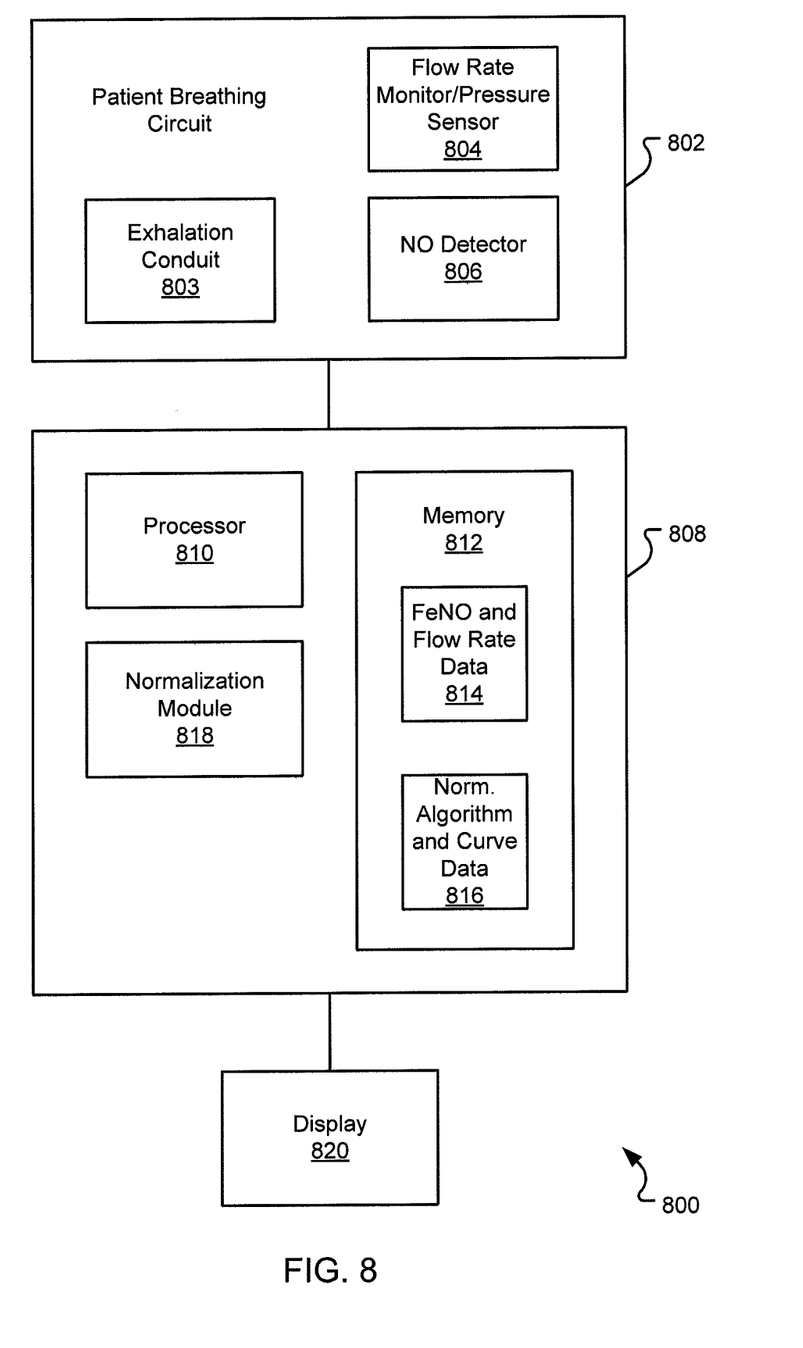
FIG. 8 is a functional block diagram illustrating components in an embodiment of an NO monitoring system capable of performing the methods described herein.

The methods described above may be used with, or adapted for use with, any NO measurement system known in the art. An example of such a system is illustrated in FIG. 8. Such systems 800 typically comprise a device 802 into which the subject exhales, sometimes referred to as the patient breathing circuit 802, coupled to an NO detector 806. In the embodiment illustrated the patient breathing circuit 802 includes a conduit 803 through which the exhaled breath travels. The system 800 also includes a flow rate monitor 804 which may take the form of a means 804 for measuring pressure which is in flow communication with the conduit, and preferably provides an instantaneous measure of the pressure in conduit. In an embodiment, the instantaneous flow rate/pressure measurement may be displayed to the subject so that the subject can monitor and adjust his/her exhalation pressure and thus adjust the exhalation flow rate to match the desired level.

NO Detection may be performed using one or more of mass spectroscopy, or electronic, optical, or acoustic vapor sensors 806. Sensor(s) 806 may include at least one sensor 806 selected from the group consisting of surface acoustic wave sensors, shear horizontal wave sensors, flexural plate wave sensors, quartz microbalance sensors, conducting polymer sensors, dye-impregnated polymer film on fiber optic detectors, conductive composite sensors, chemiresistors, chemiluminescence, metal oxide gas sensors, electrochemical gas detectors, chemically sensitive field-effect transistors, and carbon black-polymer composite devices. The sensor(s) 806 may be removable and/or replaceable.

In the embodiment illustrated in FIG. 8, an analysis module 808 is provided. The analysis module 808 may be contained in the same housing as the patient breathing circuit 802 or a separate housing as shown. The analysis module 808 is provided with a processor 810 capable of receiving the data from the NO detector 806 and flow rate monitor 804, performing the calculations described herein, and outputting the final FeNO value or results of the method 700 to a display device 820. Depending on how one of skill in the art chooses to implement the system 800, the processor may be a purpose-built electronic circuit containing any combination of hardware, software and firmware or, alternatively, may include an off-shelf or general purpose processor and other components that can execute software to perform the functions described herein. As described herein, the system 800 will be described in terms of a general-purpose processor that executes at least one software program in order to perform the functions described.

Processor 810 also may include storage of local files and/or other plug-in programs (not shown) that are run through or interact with the components of the patient breathing circuit 802. Processor 810 also may be connectable to one or more other devices such as a computing device, computing network or the display 820. Local files may be stored in a data storage module 812, discussed below, or alternatively may be considered part of the processor 810.

The analysis module 808 includes at least one data storage module containing computer-readable media as illustrated by the memory 812. Computer-readable media are capable of storing information that can be interpreted by the processor 810. This information may be data or may take the form of computer-executable instructions such as software applications.

In the embodiment shown, the memory 812 may be a mass storage device and its associated computer-readable media, and may provide volatile and/or non-volatile storage for the processor 810 and other components of the system 800. Although the description of computer-readable media contained herein refers to a mass storage device, such as a hard disk or CD-ROM drive, it should be appreciated by those skilled in the art that computer-readable media can be any available media that can be accessed by the processor 810.

By way of example, and not limitation, computer-readable media may comprise computer storage media and communication media. Computer storage media includes volatile and non-volatile, removable and non-removable media implemented in any method or technology for storage of information such as computer-readable instructions, data structures, program modules or other data. Computer storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system 800.

In the embodiment shown, the memory 812 stores the FeNO and flow rate data 814 generated by the NO detector 806 and the flow rate monitor 804. In addition to the generated data 814, the memory 812 also stores the information 816, such as instructions and data, necessary for the processor 810 to normalize the FeNO and flow rate data 814 as described above. This information 816 may include a computer-executable software application as well as information (such as a look up table or mathematical formula) describing the curve illustrated in FIG. 1. The computer-executable software application may include an algorithm as described above and contain instructions that cause the system 800 to normalize the data 814 using the algorithm. In an embodiment, the algorithm may be revised periodically. In addition, different algorithms or curves may be provided for subjects in different demographic groups.

FIG. 8 also illustrates the system 800 as including a normalization module 818. The normalization module 818 illustrates the functional elements that work together to perform the normalization method on the FeNO and flow rate data 814. Thus, in an embodiment, the normalization module 818 represents a software application that when executed by the processor 810 normalizes the data. In an alternative embodiment, the normalization module 818 represents an electronic circuit that performs the normalization. Thus, in an embodiment, the normalization module 818 may not be identifiable as a separate component from the processor and memory.

The following examples are included to demonstrate example embodiments of the invention. It should be appreciated by those of skill in the art that the techniques disclosed in the examples which follow represent techniques discovered by the inventors to function well in the practice of the invention, and thus can be considered to constitute relevant examples for its practice. However, those of skill in the art should, in light of the present disclosure, appreciate that many changes can be made in the specific embodiments which are disclosed and still obtain a like or similar result without departing from the spirit and scope of the invention.

While the above is a complete description of the preferred embodiments of the invention, various alternatives, modifications, and equivalents may be used. Therefore, the above description should not be taken as limiting the scope of the invention which is defined by the appended claims.

I claim:

1. A method performed by a nitric oxide (NO) monitoring system of determining exhaled nitric oxide (FENO) from a patient, the method comprising:
   collecting, by a patient breathing circuit, exhaled gases from the patient;
   measuring an exhalation flow rate of the exhaled gases as a function of time;
   determining an average exhalation flow rate of the exhaled gases based on the measured exhalation flow rate as a function of time;
   calculating a baseline correction factor that is a function of the measured FeNO concentration at the average exhalation flow rate and an FeNO concentration for a healthy person at the average exhalation flow rate;
   normalizing the measured FeNO concentration using the baseline correction factor to obtain a normalized FeNO;
   adjusting the normalized FeNO to a selected flow rate; and
   scaling back the normalized FeNO using the baseline correction factor to determine the FeNO of the patient.

2. The method of claim 1 wherein measuring an FeNO concentration comprises measuring FeNO concentration as a function of time.

3. The method of claim 1 wherein measuring an FeNO concentration comprises collecting a sample of exhaled gases and thereafter measuring FeNO concentration of the sample.

4. The method of claim 2 further comprising collecting the exhaled gases as a sample and thereafter measuring an FeNO concentration of the sample.

5. The method of claim 4 wherein the sample is collected in a bag.

6. The method of claim 4 wherein the sample is collected in a cylinder with a piston.

7. The method of claim 1 wherein adjusting the normalized FeNO is based on a range around the selected flow rate.

8. The method of claim 7 wherein the selected flow rate is approximately 50 ml/sec.

9. A nitric oxide (NO) monitoring system comprising:
   at least one processor; and
   at least one memory, communicatively coupled to the at least one processor and storing instructions that, when executed by the processor, cause the NO monitoring system to perform a method of determining exhaled nitric oxide (FeNO) for a subject, the method comprising:
   collecting exhaled gases from the subject;
   measuring FeNO in the collected exhaled gases;
   measuring a flow rate of the exhaled gases as a function of time;
   determining an average flow rate of the exhaled gases based on the measured flow rate of exhaled gases as a function of time;
   calculating a baseline correction factor "X" according to the formula:
   $X = A/B$ where A is the measured FeNO at the average flow rate; and B is FeNO for a normal subject at the average flow rate;
   normalizing the measured FeNO using the baseline correction factor X to obtain a normalized FeNO;
   adjusting the normalized FeNO to a selected flow rate; and
   scaling back the normalized FeNO using the baseline correction factor;
   thereby determining FeNO for the subject.

10. The system of claim 9 wherein the selected flow rate is about 50 ml/sec.

11. The system of claim 9 wherein the exhaled gases are exhaled at a substantially constant flow rate.

12. The system of claim 11 wherein the substantially constant flow rate is based at least in part on a standard.

13. The system of claim 11 wherein the substantially constant flow rate is about 50 ml/sec±10 ml/sec.

* * * * *